United States Patent [19]
Nakayama et al.

[11] Patent Number: 5,827,669
[45] Date of Patent: Oct. 27, 1998

[54] SHEETS, KITS AND METHODS FOR DETECTING ANTIGENS OR ANTIBODIES

[75] Inventors: Mikio Nakayama, Chiba-ken; Tadahiko Kitano, Tokyo; Ayumi Mitoh, Tokyo; Tetsuro Ogawa, Tokyo; Tsuneo Hiraide, Tokyo, all of Japan

[73] Assignees: Nakayama, Mikio, Chiba-ken; Kitano, Tadahiko; Asahi Kogaku Kogyo Kabushiki Kaisha, both of Toyko, all of Japan

[21] Appl. No.: 746,485

[22] Filed: Nov. 12, 1996

[30] Foreign Application Priority Data

Nov. 10, 1995 [JP] Japan ................... 7-293011

[51] Int. Cl.$^6$ .................................... G01N 33/551
[52] U.S. Cl. .............. 435/7.51; 422/56; 422/57; 435/7.94; 435/7.95; 435/287.2; 435/287.7; 435/287.9; 435/969; 435/970; 435/975; 436/524; 436/808
[58] Field of Search ...................... 435/7.5, 7.94, 435/7.95, 287.2, 287.9, 969, 970, 975; 436/524, 808; 422/56, 57

[56] References Cited

U.S. PATENT DOCUMENTS

| | | | |
|---|---|---|---|
| 4,865,733 | 9/1989 | Tsuru et al. | 210/266 |
| 4,952,323 | 8/1990 | Nakabayashi et al. | 210/691 |
| 5,018,847 | 5/1991 | Ojima et al. | 350/534 |
| 5,030,611 | 7/1991 | Ogawa et al. | 502/439 |
| 5,039,408 | 8/1991 | Ichitsuka et al. | 210/198.2 |
| 5,082,566 | 1/1992 | Tagaya et al. | 210/656 |
| 5,085,781 | 2/1992 | Tsuru et al. | 210/692 |
| 5,158,756 | 10/1992 | Ogawa et al. | 423/309 |
| 5,171,440 | 12/1992 | Kawamura | 210/198.2 |
| 5,374,516 | 12/1994 | Sutton et al. | 435/5 |
| 5,540,995 | 7/1996 | Kitano et al. | 428/407 |

FOREIGN PATENT DOCUMENTS

| | | |
|---|---|---|
| 0420053 | 4/1991 | European Pat. Off. . |
| 2282548 | 4/1995 | United Kingdom . |
| 2293009 | 3/1996 | United Kingdom . |
| 8808534 | 11/1988 | WIPO . |

OTHER PUBLICATIONS

A United Kingdom Search Report issued in connection with UK Application No. GB 9623531.2.
WPI Abstract Accession No. 89–088902/12, published 1995.
WPI Abstract Accession No. 89–088903/12, published 1995.

*Primary Examiner*—David Saunders
*Attorney, Agent, or Firm*—Greenblum & Bernstein, P.L.C.

[57] ABSTRACT

A detection sheet capable of detecting an antigen or antibody in a biological fluid with a high sensitivity in a simple operation, as well as a detection kit and detection method using the detection sheet. The detection sheet comprises (a) a fibrous aggregate with carried particles of a calcium phosphate compound having an average particle diameter of about 0.01 to 200 microns and a Ca/P ratio of about 1.0 to 2.0, and (b) an avidin, streptavidin or avidin derivative from which carbohydrates have been extracted immobilized on said calcium phosphate compound. After a biotinylated antigen or antibody is bonded to the immobilized avidin, streptavidin, or avidin derivative of the detection sheet, the detection sheet is contacted with a test solution to thereby bond an antigen or antibody of the test solution to the detection sheet. The detection sheet is then contacted with a solution of labeling compound capable of being specifically bonded to the antigen or antibody of said test solution to detect the thus labeled antigen-antibody complex.

16 Claims, 2 Drawing Sheets

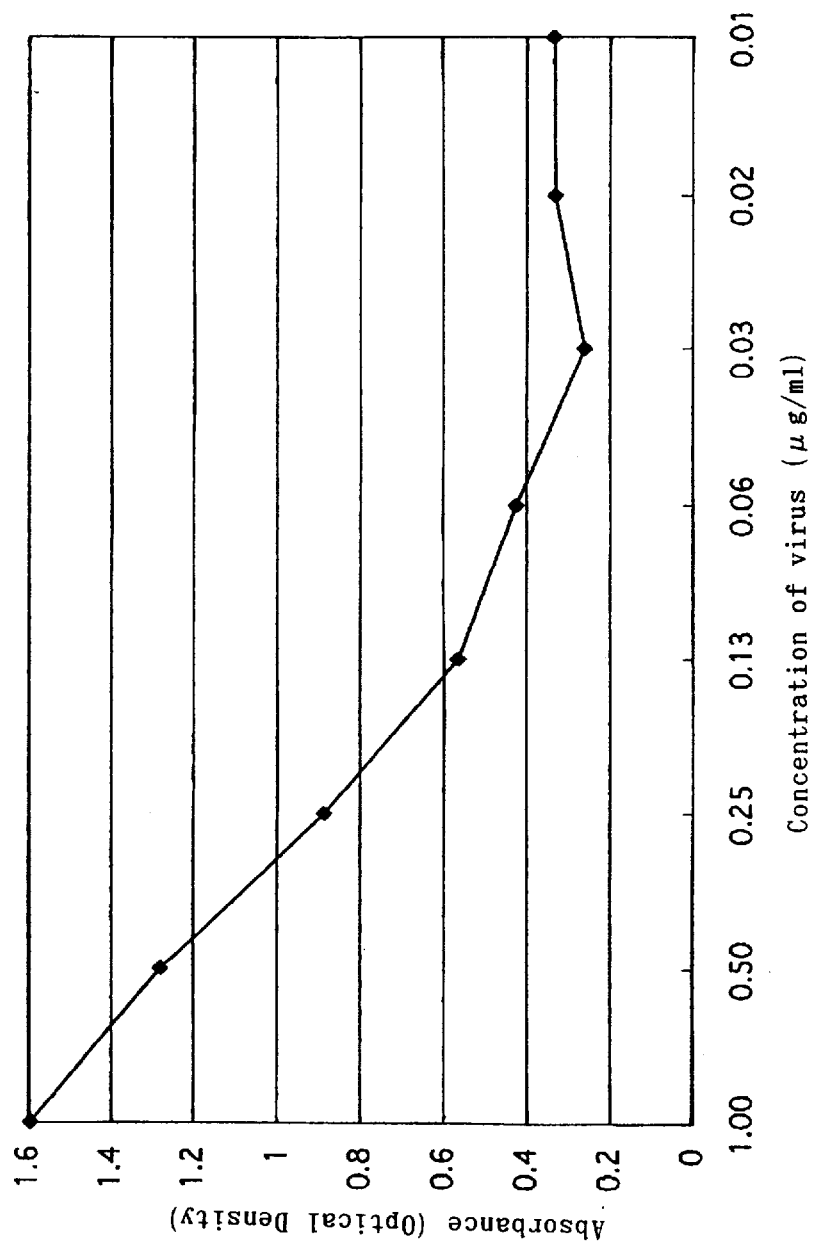

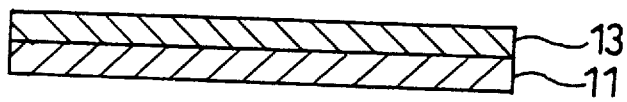
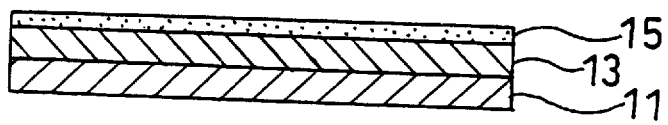
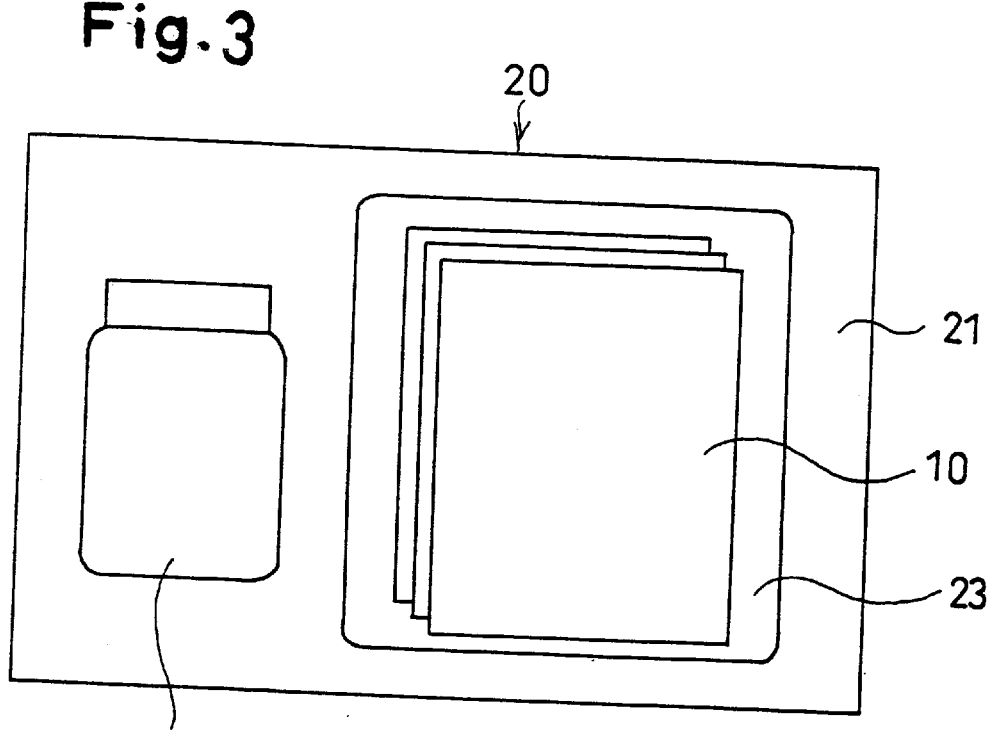

SHEETS, KITS AND METHODS FOR DETECTING ANTIGENS OR ANTIBODIES

BACKGROUND OF THE INVENTION

1. Field of the invention

The present invention relates to a detection sheet, detection kit and detection method for detecting an antigen or antibody in a biological fluid such as saliva, blood, lymph, excreta and others.

2. Description of the Related Art

In recent years, various types of clinical examination based on an antigen-antibody reaction have been carried out in a diagnostic process in hospitals or other facilities. However, such clinical examination generally requires specially designed facilities and specialized medical technicians. Therefore, it would be desirable to provide a detection sheet which enables such clinical examination to be conducted in clinics or small-scale hospitals which have neither special system or facility for said examination nor medical technician or expert. Further, it would be desirable to provide a detection sheet which enables the conduction of the examination with a high sensitivity in the diagnosis of various diseases.

As a result of zealous study, as disclosed in the U.S. patent application Ser. No. 08/524,646 filed on Sep. 8, 1995, the inventors have invented a detection sheet which comprises an antigen or antibody immobilized on a paper or nonwoven fabric having carried thereon particles of a calcium phosphate compound such as hydroxyapatite. Since it has an excellent adsorption property for proteins and nucleic acid, the calcium phosphate compound can induce an antigen-antibody reaction as a result of adsorption of the antigen or antibody on the particles thereof.

However, the inventors have recently found that the calcium phosphate compound exhibits insufficient adsorptivity for acidic proteins, and it suffers from bad orientation in the adsorption of antibodies, because the antibodies can be adsorbed in their different sites, for example, the Fab fragment portion of the antibody can be sometimes adsorbed by said compound. In order to solve these problems, the inventors have further continued their research and development to find an immobilizing method which is effective in the immobilization of an antigen or antibody which is difficult to adsorb by the calcium phosphate compound itself and a bonding method which is effective to bond an antibody to the calcium phosphate compound.

SUMMARY OF THE INVENTION

The object of the present invention is to provide a detection sheet, detection kit and detection method which can solve the above-mentioned problems and accordingly can detect an antigen or antibody contained in a biological fluid with a high sensitivity and in a simplified operation.

According to one aspect of the present invention, there is provided a detection sheet for detecting an antigen or antibody contained in a biological fluid, which comprises (a) a fibrous aggregate with the carried particles of a calcium phosphate compound having an average particle diameter of about 0.01 to 200 microns and a Ca/P ratio of about 1.0 to 2.0 and (b) an avidin, streptavidin or avidin derivative from which carbohydrates have been extracted immobilized on the calcium phosphate particles. In one preferred embodiment of the present invention, the present detection sheet can be provided as the sheet in which the immobilized avidin, streptavidin or avidin derivative from which carbohydrates have been extracted have a biotinylated antigen or antibody bonded thereto.

According to another aspect of the present invention, there is provided a detection kit for use in the detection of an antigen or antibody in a biological fluid, which comprises (A) a detection sheet comprising (a) a fibrous aggregate with the carried particles of a calcium phosphate compound having an average particle diameter of about 0.01 to 200 microns and a Ca/P ratio of about 1.0 to 2.0 and (b) an avidin, streptavidin or avidin derivative from which carbohydrates have been extracted immobilized on said fibrous aggregate, said avidin, streptavidin or derivatives thereof having a biotinylated antigen or antibody bonded thereto, and (B) a solution of labeling compound capable of being specifically bonded with said antigen or antibody.

According to still another aspect of the present invention, there is provided a method for detecting an antigen or antibody in a test solution, which comprises the steps of:

contacting a detection sheet comprising (a) a fibrous aggregate with the carried particles of a calcium phosphate compound having an average particle diameter of about 0.01 to 200 microns and a Ca/P ratio of about 1.0 to 2.0 and (b) an avidin, streptavidin or derivatives thereof immobilized on the calcium phosphate particles the avidin, streptavidin or derivatives thereof having a biotinylated antigen or antibody bonded thereto, with a test solution to thereby bond the antigen or antibody in said test solution to said detection sheet, and further contacting said detection sheet containing the bonded antigen or antibody of said test solution with a solution of a labeling compound capable of being specifically bonded with said antigen or antibody of said test solution to thereby detect the labeled antigen-antibody complex.

In the present detection sheet, detection kit and detection method, it is preferred that the fibrous aggregate used as a base of the detection sheet has a reinforcing film or sheet applied to one surface thereof.

As described above and will be further appreciated from the following description of the preferred embodiments thereof, the present invention is based on the finding that satisfactory detection of antigens and antibodies can be attained if an avidin, streptavidin or derivatives thereof are previously adsorbed and immobilized on a calcium phosphate compound carried on a fibrous aggregate.

Using the detection sheet of the present invention, it becomes possible to rapidly detect an antigen or antibody in a biological fluid, with a high detection sensitivity, and with simplified steps of operation. Further, in the present detection process, there is no restriction concerning types of the antigen or antibody to be immobilized on the detection sheet, and there is no longer a problem concerning defective orientation of the adsorption of the antigen or antibody onto the calcium phosphate compound. In addition, using the present detection sheet, it becomes possible to provide a low-cost and high-sensitivity detection kit, and thus enabling easy detection of the antigen or antibody to be conducted at clinics or small-scale hospitals not employing experts such as medical technicians.

The present disclosure relates to subject matter contained in Japanese Patent Application No. 7-293011 (filed on Nov. 10, 1995) which is expressly incorporated herein by reference in its entirety.

BRIEF DESCRIPTION OF THE DRAWINGS

FIG. 1 is a graph of the concentration of virus versus absorbance showing the results of rotavirus detection carried out in the appended working example;

FIG. 2A shows a detection sheet made by filler-incorporation method and FIG. 2B shows a detection sheet made by filler-coating method; and, FIG. 3 shows a detection kit.

DESCRIPTION OF THE PREFERRED EMBODIMENTS

In the practice of the present invention, an avidin, streptoavidin or derivatives thereof are adsorbed on a calcium phosphate compound. The derivatives of the avidin and streptavidin include the avidins from which a sugar chain portion was excluded, and non-restrictive examples thereof are NeuraAvidin, UltrAvidin and the like.

The calcium phosphate compound and particularly particles thereof carried on the fibrous aggregate are used as an agent for adsorbing and immobilizing the avidin, streptavidin or derivatives thereof. The calcium phosphate compounds used herein are not restricted, insofar as they show a Ca/P ratio in the range of about 1.0 to 2.0, and accordingly they include a wide variety of calcium phosphate compounds. For example, one or more of $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca_4O(PO_4)_2$, and $CaHPO_4$ may be used as the calcium phosphate compounds. Among these calcium phosphate compounds, hydroxyapatite and tricalcium phosphate are preferably used, and the most preferred one is a calcium phosphate compound which contains hydroxyapatite as a principal component thereof. When fluoroapatite is used as the calcium phosphate compound, it is preferred that a content of fluorine in all the calcium phosphate compounds used is not more than 5% by weight, because compounds having a fluorine content above 5% by weight can exhibit an undesirable elution of fluorine. These calcium phosphate compounds may be produced by any conventional method including a wet process, a dry process and other processes.

The particles of the calcium phosphate compound can be produced by using any conventional granulation method. For example, they can be produced by spray-drying a slurry of the calcium phosphate compound and then calcinating the dried product to obtain the intended particles of the calcium phosphate compound. Preferably, sieve and other separation means may be used to select the particles of the calcium phosphate compound having the predetermined range of the particle size depending on the intended use of the particles.

It is preferred that the particles of the calcium phosphate compound have an average particle diameter of about 0.01 to 200 microns. Average particle diameters of less than 0.01 microns tends to cause an aggregation of the particles, thereby inhibiting formation of the uniformly carried particles on the fibrous aggregate, while the average particle diameters of more than 200 microns tend to be difficult to carry on the fibrous aggregate, in particular nonwoven fabrics, thereby causing a notably reduced carrying capacity of the particles on the fibrous aggregate.

Further, the particles of the calcium phosphate compound are preferably porous particles. More preferably, the porous particles comprise agglomerated primary particles having a specific surface area of not less than 10 $m^2/g$ and pore size of about 500 to 1000 angstroms. The specific surface area should preferably be more than 10 $m^2/g$, to ensure a satisfactory adsorptivity. In addition, in order to attain introduction of the adsorbed proteins and other substances into pores or cells of the particles, it is preferred that the porous particles contain pores or cells having the above-defined pore size of about 500 to 1000 angstroms. The porous particles of the calcium phosphate compound can be produced by using any conventional method.

In practicing of the present invention, a fibrous aggregate is used as a carrier for the above-described particles of the calcium phosphate compound. The fibrous aggregate used herein includes a wide variety of sheet-like fibrous materials, and typical and nonrestrictive examples of useful fibrous aggregate include papers and nonwoven fabrics. The nonwoven fabrics may be made either of naturally occurring materials or synthetic materials.

When the particles of the calcium phosphate compound are carried on paper as a fibrous aggregate, the paper carried with said particles can be produced, for example, by using particles of the calcium phosphate compound as a filler and incorporating this filler in the paper making material or the resulting paper in accordance with an internal addition or incorporation method. Alternatively, the calcium phosphate particles may be applied via a coating method. If the filler-incorporation method is used in the production of the carried paper, particles of the calcium phosphate compound and other additives can be added to the paper making material which, after thorough mixing, is passed through a conventional paper making machine to produce the carried paper. Alternatively, if the filler-coating method is used, particles of the calcium phosphate compound can be used in combination with a binding agent, and then the mixture can be coated on the raw paper to produce the carried paper. The binding agent used herein is not restrictive, and typical examples thereof include sodium polyacrylate, polyvinylalcohol, latex, polyacrylic acid, polyethyleneoxide, carboxymethylcellulose, polyester and the like.

When the particles of the calcium phosphate compound are carried on a nonwoven fabric as a fibrous aggregate, similar methods can be used as in the above-described production of the carried paper. More preferably, the carried nonwoven fabric can be produced by applying particles of calcium phosphate compound on at least one surface of the nonwoven fabric made of the raw fibers, at least a part of which fibers consists of thermoplastic polymeric fibers, in a wet process or a dry process. After formation of the carried nonwoven fabric, a thermal treatment is made to soften at least a surface portion of the thermoplastic polymeric fibers in the nonwoven fabric, thereby fixing the particles of the calcium phosphate compound to said surface portion of the polymeric fibers.

In the production of the fibrous aggregate with carried particles of the calcium phosphate compound, the amount of particles of the calcium phosphate compound to be carried is generally in the range of 1 to 65% by weight of the fibrous aggregate, preferably in the range of 5 to 50% by weight. If the amount of the carried particles of the calcium phosphate compound is less than 1% by weight, it becomes difficult to adsorb the avidin, streptoavidin or derivatives thereof on said particles. Contrary to this, if it exceeds 65% by weight, expenses can be increased, because the amount of the avidin, streptoavidin or derivatives thereof is increased.

In the thus produced fibrous aggregate with carried particles, at least a surface portion of the fibrous aggregate, as described above, contains a layer of the calcium phosphate compound. Since the calcium phosphate compound can exhibit a higher adsorption function against the avidin, streptavidin or derivatives thereof, i.e. one of the proteins, said calcium phosphate compound layer can adsorb and immobilize these specific proteins thereon. Immobilization of the avidin, streptavidin or derivatives thereof onto the fibrous aggregate with the carried calcium phosphate compound can be achieved by using an aqueous solution of said avidin, streptavidin or derivatives thereof by using dip coating, brush coating, spray coating and other conventional coating methods.

The amount of avidin, streptavidin or derivatives thereof to be immobilized on the fibrous aggregate may be widely varied depending upon the type and amount of the calcium phosphate compound carried on said fibrous aggregate. For example, if the fibrous aggregate is a nonwoven fabric and it carries 3.0 g/m$^2$ of hydroxyapatite, the amount of said specific proteins to be immobilized is preferably 5 to 20 mg/m$^2$, more preferably about 10 mg/m$^2$. Amount of less than 5 mg/M$^2$ tend to produce many unadsorbed sites of hydroxyapatite, and amounts of more than 20 mg/m$^2$ is economically undesirable, because these proteins are expensive.

The avidin, streptavidin or derivatives thereof have a notably high affinity to a biotin, and the biotin can be easily bonded with antibodies and many enzymes. Based on these specific properties, there is provided a detection sheet in which the antigen or antibody was immobilized with a good and right orientation on the fibrous aggregate. The good orientation is the result of a reaction between the avidin, streptoavidin or derivatives thereof immobilized in the above-mentioned method and the biotinylated antigen or antibody. Using the thus provided detection sheet, an antigen or antibody included in a test solution can be easily detected with a high sensitivity by contacting the detection sheet with the test solution followed by contacting with a solution of labeling compound.

In practicing the present invention, if necessary, before or after the above-mentioned reaction between the specific proteins, i.e., avidin, streptavidin or derivatives thereof and the biotinated antigen or antibody, sites of the particles of the calcium phosphate compound carried on the fibrous aggregate, to which sites the avidin, streptavidin or derivatives thereof have not been adsorbed, may be treated with a blocking agent in order to mask said avidin-, or streptavidin-unadsorbed sites of the carried particles. Note, however, that the blocking process is not essential to the present invention and accordingly it may be omitted, if desired.

Further, in order to improve handling of the detection sheet, the detection sheet may additionally comprise a reinforcing film (or sheet) 11 applied or preferably adhered to one surface of a fibrous aggregate free of calcium phosphate coating. In FIG. 2A, the detection sheet made by filler-incorporation method is comprised of a reinforcing film 11 applied or adhered to fiber aggregate 13. In FIG. 2B, the detection sheet made by the filler-coating method is comprised of a calcium phosphate coating 15 carried on a fiber aggregate 13, and a reinforcing film 11 is applied or adhered to the opposite side of the fiber aggregate 13. The reinforcing film or sheet may be produced from various materials, and suitable examples of the film- or sheet-forming materials include paper or plastics. The reinforcing film or sheet may be a laminate, if desired.

In addition to the detection sheet, according to the present invention, there is provided a detection kit for detecting an antigen or antibody by associating the above-described detection sheet of the present invention with a solution of a labeling compound. The detection sheet 10 is enclosed in a bag 23, which together with the solution of labeling compound 25, is stored in a box.

The labeling compound 25 used in the preparation of the detection kit 20 can be selected from various labeling compounds well-known in the field of this technology. Typical examples of useful labeling compounds include enzyme-labeled antibodies or antigens, isotope-labeled antibodies or antigens and others, which are able to be specifically bonded with an antigen or antibody in a test medium. It is preferred to use the enzyme-labeled antibodies or antigens as the labeling compound, because they do not require any specially designed installations and thereby simplify the detection operation. Further, when the enzyme-labeled antibodies or antigens are used as the labeling compound, it becomes possible to conduct the detection of the antigen or antibody by using a substrate for said labeling enzyme capable of indicating a color at a wavelength of visible or ultraviolet radiations so that said antigen or antibody can be easily detected by using a simple method such as visual inspection, determination of an absorbance and the like. Suitable combinations of the enzyme as the labeling compound and the substrate includes, for example:

| enzyme | substrate |
|---|---|
| alkaline phosphatase | BCIP and NBT: 5-Bromo-4-chloro-3-indoyl phosphate/nitroblue tetrazolium |
| alkaline phosphatase | DNP: P-Nitrophenyl phosphate, Disodium |
| horseradish peroxidase | OPD: O-Phenylenediamine |
| horseradish peroxidase | DAB: 3,3'-Diaminobezide Tetrahydrochloride |
| horseradish peroxidase | 4CN |
| β-D-galactosidase | pNPG |
| β-D-galactosidase | X-gal |

The detection sheet and detection method according to the present invention can be principally used to ascertain whether an antigen or antibody is contained in a test medium. Further, they may be utilized in an quantitative analysis of the antigen or antibody, if a comparison of the color density between the indicated colors or a determination of the absorbance is made following the detection step. The present invention will be further described with reference to working examples thereof. Note, however, that the present invention should not be restricted to these examples.

EXAMPLE 1

Porous granules of hydroxyapatite having an average grain diameter of 3.5 microns and a Ca/P ratio of 1.67 were applied to a nonwoven fabric having a thickness of 0.2 mm and a size of 5 max 5 mm consisting of 50% by weight of polyethylene and 50% by weight of polyethylene terephthalate. The nonwoven fabric was thermally treated to produce an apatite-carried nonwoven fabric having substantially uniformly carried thereon 24% by weight of the hydroxyapatite granules. The apatite-carried nonwoven fabric was then immersed in an aqueous solution containing 5 μg/ml of avidin so that 10 mg/m$^2$ of avidin was adsorbed in the nonwoven fabric. Thereafter, a sufficient amount of biotinylated antiRota IgG antibody of rabbit was bonded to avidin on the nonwoven fabric to produce a detection sheet for use in the detection of Rotavirus.

The detection of Rotavirus was made using the resulting detection sheet in accordance with a sandwich EIA method. First, a Rotavirus antigen in the Rotavirus solution was trapped with the detection sheet. Then, an antiRotavirus-alkaline phosphatase-bonded labeling antibody of guinea pig was bonded to the Rotavirus antigen on the detection sheet, and the detection was made with reference to the coloring of the substrate for EIA, DNP. In this determination, the wavelength of light irradiated was 405 nm. The sensitivity of the detection sheet was evaluated by changing a degree of the dilution of the Rotavirus antigen used. It has been found that using the present detection sheet, the detection can be made until an amount of the virus is reduced to 0.062 μg/ml. The results of the determination are plotted in FIG. 1 as a graph showing the relation between the concentration of virus and the absorbance. The absorbance was determined on an absorption meter, Microwell system, commercially available from Organon Teknika Co.

The detection of Rotavirus was then made with the concentration of Rotavirus of 0.25 μg/ml. Satisfactory detection of the virus could be made because the absorbance was 0.95.

EXAMPLE 2

This example is a comparative example.

Porous granules of hydroxyapatite having an average grain diameter of 3.5 microns and a Ca/P ratio of 1.67 were applied to a nonwoven fabric having a thickness of 0.2 mm and a size of 5 max 5 mm consisting of 50% by weight of polyethylene and 50% by weight of polyethylene terephthalate. The nonwoven fabric was thermally treated to produce an apatite-carried nonwoven fabric having substantially uniformly carried thereon 24% by weight of the hydroxyapatite granules. Thereafter, a sufficient amount of antiRota IgG antibody of rabbit was adsorbed by the apatite-carried nonwoven fabric, and then immobilized on the nonwoven fabric by immersing the fabric in a solution of 0.05% by weight of glutaraldehyde. After immobilization of said antibody, the nonwoven fabric was immersed in a four times-diluted solution of a blocking agent containing casein, trade name "Block Ace" commercially available from Snow Brands Milk Products Co., Ltd. in order to selectively mask the antiRota IgG antibody-unadsorbed sites of the fabric. The comparative detection sheet was thus produced.

The detection of Rotavirus was made using the comparative detection sheet in accordance with the manner similar to that of Example 1. When the concentration of the Rotavirus was 0.25 μg/ml, the virus could not be detected because the absorbance was 0.01.

We claim:

1. A detection sheet for detecting an antigen or antibody in a biological fluid, which comprises (a) a fibrous aggregate with carried particles of a calcium phosphate compound having an average particle diameter of about 0.01 to 200 microns and a Ca/P ratio of about 1.0 to 2.0 and (b) an avidin, streptavidin or avidin derivative from which carbohydrates have been extracted immobilized on said calcium phosphate compound.

2. A detection sheet according to claim 1 in which said immobilized avidin, streptavidin or derivatives thereof have a biotinylated antigen or antibody bonded thereto.

3. A detection sheet according to claim 1 in which said fibrous aggregate has a reinforcing film or sheet applied to one surface thereof.

4. A detection sheet according to claim 1 in which said carried particles comprise agglomerated primary particles having a specific surface area of not less than 10 m²/g.

5. A detection sheet according to claim 1 in which said carried particles comprise agglomerated primary particles having a pore size of about 500 to 1000 angstroms.

6. A detection sheet according to claim 1 in which amount of said particles of said calcium phosphate compound to be carried is generally in range of 1 to 65% by weight of the fibrous aggregate.

7. A detection kit for use in the detection of an antigen or antibody in a biological fluid, which comprises (A) a detection sheet comprising (a) a fibrous aggregate with carried particles of a calcium phosphate compound having an average particle diameter of about 0.01 to 200 microns and a Ca/P ratio of about 1.0 to 2.0 and (b) an avidin, streptavidin or avidin derivative from which carbohydrates have been extracted immobilized on said calcium phosphate compound, said avidin, streptavidin or avidin derivative from which carbohydrates have been extracted having a biotinylated antigen or antibody bonded thereto, and (B) a solution of labeling compound capable of being specifically bonded with said antigen or antibody.

8. A detection kit according to claim 7 in which said fibrous aggregate has a reinforcing film or sheet applied to one surface thereof.

9. A detection kit according to claim 7 in which said carried particles comprise agglomerated primary particles having a specific surface area of not less than 10 m²/g.

10. A detection kit according to claim 7 in which said carried particles comprise agglomerated primary particles having a pore size of about 500 to 1000 angstroms.

11. A detection kit according to claim 7 in which amount of said particles of said calcium phosphate compound to be carried is generally in range of 1 to 65% by weight of the fibrous aggregate.

12. A method for detecting an antigen or antibody in a test solution, which comprises the steps of:

contacting a detection sheet comprising (a) a fibrous aggregate with carried particles of a calcium phosphate compound having an average particle diameter of about 0.01 to 200 microns and a Ca/P ratio of about 1.0 to 2.0 and (b) an avidin, streptavidin or avidin derivative from which carbohydrates have been extracted immobilized on said fibrous aggregate, said avidin, streptavidin or avidin derivative from which carbohydrates have been extracted having a biotinylated antigen or antibody bonded thereto, with a test solution to thereby bond the antigen or antibody in said test solution to said detection sheet, and contacting said detection sheet containing the bonded antigen or antibody of said test solution with a solution of a labeling compound capable of being specifically bonded with said antigen or antibody of said test solution to thereby detect a labeled antigen-antibody complex.

13. A method for detecting an antigen or antibody in a test solution according to claim 12 in which said carried particles comprise agglomerated primary particles having a specific surface area of not less than 10 m²/g.

14. A method for detecting an antigen or antibody in a test solution according to claim 12 in which said carried particles comprise agglomerated primary particles having a pore size of about 500 to 1000 angstroms.

15. A method for detecting an antigen or antibody in a test solution according to claim 12 in which amount of said particles of said calcium phosphate compound to be carried is generally in range of 1 to 65% by weight of the fibrous aggregate.

16. A method for detecting an antigen or antibody according to claim 12 in which said fibrous aggregate has a reinforcing film or sheet applied to a surface thereof.

* * * * *